(12) United States Patent
Reed (10) Patent No.: US 10,160,813 B2
(45) Date of Patent: Dec. 25, 2018

(54) TISSUE PLASMINOGEN ACTIVATOR ANTIBODIES AND METHODS OF USE

(71) Applicant: University of Tennessee Research Foundation, Knoxville, TN (US)

(72) Inventor: Guy Reed, Knoxville, TN (US)

(73) Assignee: UNIVERSITY OF TENNESSEE RESEARCH FOUNDATION, Knoxville, TN (US)

( * ) Notice: Subject to any disclaimer, the term of this patent is extended or adjusted under 35 U.S.C. 154(b) by 317 days.

(21) Appl. No.: 14/762,601

(22) PCT Filed: Jan. 22, 2014

(86) PCT No.: PCT/US2014/012555
§ 371 (c)(1),
(2) Date: Jul. 22, 2015

(87) PCT Pub. No.: WO2014/116706
PCT Pub. Date: Jul. 31, 2014

(65) Prior Publication Data
US 2015/0353647 A1   Dec. 10, 2015

Related U.S. Application Data

(60) Provisional application No. 61/755,298, filed on Jan. 22, 2013.

(51) Int. Cl.
*C07K 16/40* (2006.01)
*G01N 33/573* (2006.01)
*G01N 33/86* (2006.01)
*A61K 39/00* (2006.01)

(52) U.S. Cl.
CPC .......... *C07K 16/40* (2013.01); *G01N 33/573* (2013.01); *G01N 33/86* (2013.01); *A61K 2039/507* (2013.01); *C07K 2317/33* (2013.01); *C07K 2317/76* (2013.01); *C07K 2317/92* (2013.01); *G01N 2333/96433* (2013.01)

(58) Field of Classification Search
None
See application file for complete search history.

(56) References Cited

U.S. PATENT DOCUMENTS

| 5,004,802 A | 4/1991 | Kluft |
| 5,102,787 A * | 4/1992 | Sasamata ............... C07K 16/40 435/13 |
| 5,225,540 A * | 7/1993 | Reilly ............... A61K 38/49 424/145.1 |
| 6,136,548 A | 10/2000 | Anderson |
| 2011/0091436 A1 | 4/2011 | Orbe Lopategui et al. |

FOREIGN PATENT DOCUMENTS

| EP | 0178105 A2 | 4/1986 | |
| EP | 0190711 A2 * | 8/1986 | ............ C07K 16/40 |
| EP | 0339302 A1 * | 11/1989 | ............ G01N 33/86 |
| EP | 0339505 A2 | 11/1989 | |

OTHER PUBLICATIONS

Hashimoto et al., Thromb Haemost. May 2003;89(5):820-5.*
Vaughan et al., Nat Biotechnol. Mar. 1996;14(3):309-14.*
Janeway et al.,Immunobiology, 3$^{rd}$ edition, 1997, Garland Press, pp. 3:1-3:11.*
Rudikoff et al., Proc Natl Acad Sci U S A. Mar. 1982;79(6):1979-83.*
Zacharias et al., Thromb Haemost. Jan. 23, 1992;67(1):88-94.*
Wark, K.L., Microbiology Australia, vol. 27, issue 2, May 2006, pp. 74-75.*
Jankun, Jet al. Highly Stable Plasminogen Activator Inhibitor Type One (VLHL PAI-1) Protects Fibrin Clots From Tissue Plasminogen Activator-Mediated Fibrinolysis. International Journal of Molecular Medicine. 2007, vol. 20; pp. 683-687.
Kurokawa, T et al. Characterization of Monoclonal Antibodies Against Human Tissue Plasminogen Activator (tPA): Quantitation of Free tPA in Human Cell Cultures by an ELISA. Journal of Biochemistry. 1991, vol. 1 09; pp. 217-222.
Imubind tPA ELISA User Manual [online]. American Diagnostica. 2012.
Reed, G. Two Monoclonal Antibodies That Specifically Inhibit Plasminogen Activated Induced by TPA. Jul. 14, 2013.

* cited by examiner

*Primary Examiner* — Michael Szperka
(74) *Attorney, Agent, or Firm* — Baker Donelson (57) ABSTRACT

A molecule that binds specifically to a human tissue plasminogen activator (TPA) or a TPA mutant is provided. The molecule having sub-nanomolar affinity to inhibit fibrin-dependent plasminogen activation with an IC50<5 nM, to inhibit degradation of human fibrin clots without affecting TPA amidolytic activity or non-fibrin-dependent activation, and the amino acid sequence of the TPA mutant is at least 65% identical to SEQ ID NO: 1 or SEQ ID NO: 2. Further provided is a method for treating systemic bleeding and brain hemorrhage after TPA treatment in a patient in need of such treatment. The method comprises administering to said patient an effective amount of the molecule, wherein the molecule selectively inhibits fibrin-augmented plasminogen activation in the patient.

15 Claims, 5 Drawing Sheets
Specification includes a Sequence Listing.

FIG. 5 (Con't)

C

D

E

TISSUE PLASMINOGEN ACTIVATOR ANTIBODIES AND METHODS OF USE

CROSS REFERENCE TO RELATED APPLICATIONS

This application is a § 371 National State Application of PCT/US2014/012555 filed Jan. 22, 2014, which claims priority to U.S. Provisional Patent Application 61/755,298 filed Jan. 22, 2013, the entirety of which are hereby incorporated by reference herein.

STATEMENT OF GOVERNMENT RIGHTS

This invention was made with Government support under Grant Number HL058496, HL097250 and NS073147 awarded by the National Institute of Health. The Government has certain rights in the invention.

FIELD OF INVENTION

The present invention provides tissue plasminogen activator antibodies and methods of their use. More particularly, the presently-disclosed invention provides a monoclonal antibody against tissue plasminogen activator and a method to inhibit brain hemorrhage and systemic bleeding after tissue plasminogen activator treatment.

BACKGROUND OF THE INVENTION

Tissue plasminogen activator (TPA or tPA) is the only effective treatment for ischemic stroke and, it also reduces mortality for patients with acute myocardial infarction. (Donnan G A, Davis S M, Parsons M W, Ma H, Dewey H M, Howells D W. How to make better use of thrombolytic therapy in acute ischemic stroke. *Nat Rev Neurol.* 2011; 7:400-409.) However, TPA treatment significantly increases the risk of serious or fatal bleeding. Intracranial bleeding after TPA therapy can be devastating and roughly 1% of patients treated with TPA for stroke will experience severely disabling or fatal hemorrhage. (Saver J L. Hemorrhage after thrombolytic therapy for stroke: the clinically relevant number needed to harm. *Stroke.* 2007; 38:2279-2283.) Similarly, 0.9-1.0% of patients given TPA for myocardial infarction develop intracranial hemorrhage and more than 50% of patients die. (Gurwitz J H, Gore J M, Goldberg R J, et al. Risk for intracranial hemorrhage after tissue plasminogen activator treatment for acute myocardial infarction. Participants in the National Registry of Myocardial Infarction 2. *Ann Intern Med.* 1998; 129:597-604.) Although bleeding complications are often seen in older adults, children are also at significant risk of bleeding from TPA. (Gupta A A, Leaker M, Andrew M, et al. Safety and outcomes of thrombolysis with tissue plasminogen activator for treatment of intravascular thrombosis in children. *J Pediatr.* 2001; 139: 682-688.) Fear of bleeding complications has diminished the therapeutic administration of TPA to patients who might otherwise benefit. (Saver J L. Hemorrhage after thrombolytic therapy for stroke: the clinically relevant number needed to harm. *Stroke.* 2007; 38:2279-2283.)

Once TPA-induced hemorrhage occurs there is no specific TPA inhibitor or antidote available to treat the bleeding. In an effort to restore coagulation, patients are frequently given cryoprecipitate, fresh frozen plasma, and platelets without conclusive evidence of efficacy. (Morgenstern L B, Hemphill J C, 3rd, Anderson C, et al. Guidelines for the management of spontaneous intracerebral hemorrhage: a guideline for healthcare professionals from the American Heart Association/American Stroke Association. *Stroke.* 2010 41:2108-2129.) Antifibrinolytic agents such as, tranexamic acid, ε-aminocaproic acid, aprotinin and novel plasmin inhibitors have also been used, but to a limited extent. Unfortunately, these agents not only inhibit the plasminogen (Pg) activation system, but also interfere with other molecular pathways. For example, aprotinin affects plasmin activity as well as the kallikrein system and, has been associated with severe allergies. (Munoz J J, Birkmeyer N J, Birkmeyer J D, O'Connor G T, Dacey U. Is epsilon-aminocaproic acid as effective as aprotinin in reducing bleeding with cardiac surgery a meta-analysis. *Circulation.* 1999; 99:81-89.)

The mechanisms responsible for TPA bleeding are still poorly understood. By comparison to streptokinase, activation of Pg by TPA is markedly amplified by fibrin and this distinguishing property of TPA was predicted to increase fibrinolysis without increasing bleeding complications. However, excessive plasmin generation by TPA may degrade clotting factors in the circulation which affects coagulation and may enhance bleeding in vivo. TPA is a multidomain molecule that functions through both catalytic and non-catalytic interactions. There is experimental evidence that non-catalytic actions of TPA (e.g., those not causing plasminogen activation) cause breakdown of the blood brain barrier and are responsible for some of TPA's neurotoxic effects. As such, it is unclear whether TPA-induced brain hemorrhage requires the catalytic activity of TPA. TPA therapy is beneficial in ischemic stroke and myocardial infarction, but in some patients it is complicated by serious or fatal bleeding in the brain and at other sites. Fear of TPA-induced bleeding has limited the therapeutic use of TPA. In humans, TPA-induced hemorrhage and adverse outcomes are more frequent after prolonged ischemia. Similarly, in experimental stroke, after prolonged ischemia, TPA reproducibly causes brain hemorrhage, breakdown of the blood brain barrier and enhanced neuronal cell death.

In non-thrombotic models of stroke there is evidence that TPA may exert toxic effects through mechanisms, such as PDGF-CC cleavage, etc. that do not require plasminogen activation or affect fibrinolytic activity. (Su E J, Fredriksson L, Geyer M, et al. Activation of PDGF-CC by tissue plasminogen activator impairs blood-brain barrier integrity during ischemic stroke. *Nat Med.* 2008; 14:731-737.) Under pathological conditions like myocardial ischemia and stroke, the fibrinolytic activity of therapeutic TPA is enhanced by increased levels of circulating fibrin fragments (e.g., D-dimer), which may enhance the bleeding process. (Barber M, Langhorne P, Rumley A, Lowe G D, Stott D J. D-dimer predicts early clinical progression in ischemic stroke: confirmation using routine clinical assays. *Stroke.* 2006; 37: 1113-1115.)

SUMMARY OF THE INVENTION

This summary describes several embodiments of the presently-disclosed subject matter, and, in many cases, lists variations and permutations of these embodiments. This Summary is merely exemplary of the numerous and varied embodiments. Mention of one or more representative features of a given embodiment is likewise exemplary. Such an embodiment can typically exist with or without the feature(s) mentioned; likewise, those features can be applied to other embodiments of the presently-disclosed subject matter, whether listed in this Summary or not. To avoid excessive repetition, this Summary does not list or suggest all possible combinations of such features.

The present invention addresses these and other related needs by providing, inter alia, antibodies and antigen-binding fragments thereof that are capable of inhibiting TPA-induced fibrinolysis. This invention is based, in part, on the discovery that tissue plasminogen activator uniquely activates plasminogen through a fibrin-dependent mechanism that contributes to brain hemorrhage in ischemic stroke. Synergistic monoclonal antibodies block this action by reducing brain hemorrhage, surgical bleeding and brain cell death after TPA treatment.

In some embodiments, the presently-disclosed invention provides a molecule that binds specifically to a human tissue plasminogen activator (TPA) or a TPA mutant. The molecule has sub-nanomolar affinity to inhibit fibrin-dependent plasminogen activation with an IC50<5 nM, and the amino acid sequence of said TPA mutant is at least 65% identical to SEQ ID NO: 1 or SEQ ID NO: 2. In some embodiments, the molecule does not inhibit degradation of human fibrin clots without affecting TPA amidolytic activity or non-fibrin-dependent activation, In some embodiments, the present invention provides a method for treating systemic bleeding, brain hemorrhage and/or stroke after TPA treatment in a patient in need of such treatment, which comprises administering to the patient an effective amount of the molecule as described above, wherein said molecule selectively inhibits fibrin-augmented plasminogen activation in the patient. In some embodiments, said molecule may be an antibody or an antibody-binding fragment.

The presently-disclosed invention further provides, in some embodiments, a purified or isolated antibody that specifically binds to tissue plasminogen activator (TPA) and inhibits TPA-induced fibrinolysis of human clots. In some embodiments, the present invention discloses a purified or isolated monoclonal antibody that specifically binds to a TPA molecule to inhibit TPA-induced fibrinolysis of human clots. More specially, the isolated antibody is identified as TPA1-14 and or TPA1-23 and it selectively inhibits fibrin-augmented plasminogen activation.

In some embodiments of the present invention, a pharmaceutical composition made of an effective amount of an antibody capable of treating TPA induced systematic bleeding and hemorrhage, and a pharmaceutical carrier is contemplated.

Further provided in some embodiments of the presently-disclosed invention, is a purified or isolated antibody that binds specifically to a human tissue plasminogen activator (TPA) or a TPA mutant. In some embodiments, the amino acid sequence of said TPA mutant is at least 65% identical to SEQ ID NO: 1 or SEQ ID NO: 2. In some embodiments, the antibody has sub-nanomolar affinity to inhibit fibrin-dependent plasminogen activation with an IC50<5 nM. Yet in some embodiments, the antibody inhibits degradation of human fibrin clots without affecting TPA amidolytic activity or non-fibrin-dependent activation.

In some embodiments, the presently-disclosed invention provides a method for treating systemic bleeding, brain hemorrhage and/or stroke after TPA treatment in a patient in need of such treatment, which comprises administering to said patient an effective amount of the antibody as described above, and the antibody selectively inhibits fibrin-augmented plasminogen activation in the patient.

In some embodiments, the presently-disclosed invention provides a kit for the treatment of systemic hemorrhage after TPA treatment in a subject in need thereof. The kit comprises a purified or isolated antibody that specifically binds to TPA to inhibit TPA-induced fibrinolysis of human clots and instructions for using said antibody to treat the systemic bleeding, brain hemorrhage, and/or stroke.

Further provided, in some embodiment of the present invention, is a method for treating systemic hemorrhage after TPA treatment in a patient in need of such treatment. The method comprises administering to the patient an effective amount of at least one purified or isolated antibody capable of binding to an epitope of TPA. In some embodiments, the antibody selectively inhibits fibrin-augmented plasminogen activation in the patient. Further still, in some embodiments, the present invention provides that the at least one purified or isolated antibody is identified as TPAi-14 or TPAi-23, and TPAi-14 and TPAi-23 bind with high affinity to different epitopes on TPA.

Further still, in some embodiments of the presently-disclosed invention, is a method for identifying molecules that can inhibit TPA-induced fibrinolysis of human clots. The method includes the steps of: providing a monoclonal antibody that specifically binds to TPA and inhibits TPA-induced fibrinolysis of human clots, affixing said monoclonal antibody to a surface, providing TPA and introducing an agent to said TPA that blocks the non-specific binding regions of TPA, introducing a candidate molecule to said TPA, introducing said TPA to said monoclonal antibody, determining if said candidate molecule has bound to the epitope of the TPA where said monoclonal antibody had bound to the TPA, and identifying any candidate molecule binding to said epitope as a molecule that can inhibit TPA-induced fibrinolysis of human clots.

Advantages of the presently-disclosed subject matter will become evident to those of ordinary skill in the art after a study of the description, Figures, and non-limiting Examples in this document.

BRIEF DESCRIPTION OF THE SEVERAL VIEWS OF THE DRAWINGS

FIG. 1 includes graphs illustrating the inhibition of TPA-induced human fibrinolysis. A) Binding of monoclonal antibody (mAbs) to human TPA or BSA (control) assessed by ELISA (Methods). B) Termination of the initiation of human fibrinolysis. Fibrinolysis of human plasma clots was induced by 0.5 nM TPA in the presence of varying concentrations of a TPA-non-reactive control antibody (Ctrl), TPAi-14, TPAi-23, and a PA1-1 mutant with stabilized activity. The percent fibrinolysis was measured after 2 hrs. and the percent inhibition was calculated as described in Methods. Data represent the mean±SD of at least three independent experiments. C) Half maximum inhibitory concentration (IC50) of TPA mAbs. IC50 (mean±SD from 95% CI) was calculated with data from the dose response curve of each mAb or PAI-1 (B) as described in Methods. D) Termination of ongoing fibrinolysis. Fibrinolysis was initiated with 0.5 nM TPA as described above and inhibitors (25 nM) were added after one hour. Fibrinolysis was measured at 1 and 3 hrs. and the percent inhibition was calculated with respect to that of the control mAb.

FIG. 2 is graphs showing the comparative binding and inhibitory specificity of TPAi-14 and TPAi-23. A) TPAi-14 and TPAi-23 do not compete for binding to TPA. A competition binding ELISA was performed as described in Methods to examine whether an unlabeled mAb would inhibit the binding of an HRP-labeled mAb to TPA loaded in wells of microplate. TPAi-14 inhibited HRP-labeled TPAi-14 but not TPAi-23; similarly TPAi-23 inhibited HRP-labeled TPA-i23 but not TPAi-14. B) Binding specificity. The binding of mAbs to TPA, TPA-PAI-1 complex and BSA (control) coated wells were assessed by ELISA assay at A370 nm. For comparison, the binding of an anti-PAI-1 mAb MA-33H1F7 to TPA-PA1-1 wells as shown C) Specific inhibition of fibrinolysis by human but not mouse TPA. Fibrinolysis of human plasma clots was induced with either 0.5 nM human TPA in the presence of 5 nM anti-TPA mAb, or 2 nM mouse TPA in the presence of 100 nM TPAi-14. Fibrinolysis of mouse plasma clots was induced with either 100 nM human TPA in the presence of 100 nM anti-TPA mAb, or 16oM mouse TPA in the presence of 800 nM TPAi-14. The percentage of human or mouse fibrinolysis inhibition was measured at two hrs. after the addition of TPA. D) Specific inhibition of fibrinolysis induced by TPA but not other Pg activators. Fibrinolysis of human plasma clots was induced with either 40 nM SAK or 2.5 unit uPA in the presence of 5 nM TPA non-reactive mAb (Ctrl), anti-TPA mAbs TPAi-14 and TPAi-23, PAI-1, or anti-uPA inhibitory mAb uPA-394. The percentage of human fibrinolysis inhibition was measured at two hrs after the addition of SAK or uPA. The results represent mean±SD of at least two independent experiments.

FIG. 3 includes graphs showing the mechanism of inhibition of TPA by TPAi-14 and TPAi-23. A) TPAi-14 and TPAi-23 do not affect the amidolytic or catalytic activity of TPA with a tripeptide substrate. The cleavage of S2288 by human TPA (100 nM) was monitored at 405 nm (left panel) in the presence of 10-fold molar excess (1 µM) of a TPA non-reactive control mAb (Ctrl, open circle), TPAi-14 (solid square) or TPAi-23 (shaded triangle). The effect of mAbs on the relative TPA activity (right panel) was calculated as described in Methods and normalized with respect to the activity of Ctrl mAb. B) TPAi-14 and TPAi-23 do not affect the amidolytic or catalytic activity of TPA with a tripeptide substrate in the presence of fibrin. The amidolytic activity of 50 nM human TPA in the presence of 0.5 µM Ctrl, TPAi-14 or TPAi-23 and 0.05 mg/ml fibrin fragment was detected with S2288 assay (left panel) and the relative TPA activities (right panel) were calculated as above. C) The activation of Glu-Pg (100 nM) to plasmin with TPA (20 nM) was examined with S2251 assay in the presence of 10-fold molar excess (200 nM) of Ctrl mAb, TPAi-14, or TPAi-23. The absorbance at 405 nm was recorded (left panel). The Pg activation rate by TPA was calculated using A405 nm change per second squared over the initial period of reaction as described in Methods and normalized with respect to the rate of Ctrl mAb (right panel). The difference between Ctrl and TPAi-23 is significant (*p=0.00006). D) The activation of Glu-Pg (100 nM) to plasmin with TPA (1 nM) was examined in the presence of 10-fold molar excess (10 nM) of Ctrl, TPAi-14, or TPAi-23 and 0.05 mg/ml fibrin fragment. The differences between Ctrl and TPAi-14 (*p=0.002) or TPAi-23 (**p=0.00006) are significant. All data are representative results of mean±SD from at least three experiments.

FIG. 4 includes graphs showing synergistic inhibition of fibrinolysis by TPAi-14 and TPAi-23. A) Fibrinolysis of human plasma clots was induced with 0.5 nM TPA in the presence of TPAi-14 or TPAi-23 alone (0.5-1 nM), or their combination (0.5 nM each). The percent inhibition of fibrinolysis was measured after 2 hrs. and calculated as described in the Methods. The results represent mean±SD of at least three independent experiments. B) Fibrinolysis of human plasma clots examined as above in the presence of TPAi-14 or TPAi-23 or fractional combinations of the two agents together. The dose of TPAi-14 or TPAi-23 alone or combinations that achieved 50% fibrinolysis inhibition is depicted in the isobologram (See Berenbaum M C. The expected effect of a combination of agents: the general solution. *J Theor Bioi.* 1985; 114:413-431.) Inset showed a hypothetical isobole demonstrating synergy, additivity and antagonism.

BRIEF DESCRIPTION OF THE SEQUENCE LISTING

SEQ ID NO: 1 is an amino acid sequence of human tissue plasminogen activator with GenBank® Accession No. AAA01378.1.

SEQ ID NO: 2 is an amino acid sequence of human tissue plasminogen activator with GenBank® Accession No. AAA01895.1.

DETAILED DESCRIPTION OF THE INVENTION

The details of one or more embodiments of the presently-disclosed subject matter are set forth in this document. Modifications to embodiments described in this document, and other embodiments, will be evident to those of ordinary skill in the art after a study of the information provided in this document. The information provided in this document, and particularly the specific details of the described exemplary embodiments, is provided primarily for clearness of understanding and no unnecessary limitations are to be understood therefrom. In case of conflict, the specification of this document, including definitions, will control.

Some of the polypeptide sequences disclosed herein are cross-referenced to GENBANK® accession numbers. The sequences cross-referenced in the GENBANK® database are expressly incorporated by reference as are equivalent and related sequences present in GENBANK® or other public databases. Also expressly incorporated herein by reference are all annotations present in the GENBANK® database associated with the sequences disclosed herein.

While the terms used herein are believed to be well-understood by one of ordinary skill in the art, definitions are set forth to facilitate explanation of the presently-disclosed subject matter.

Unless defined otherwise, all technical and scientific terms used herein have the same meaning as commonly understood by one of ordinary skill in the art to which the presently-disclosed subject matter belongs. Although any methods, devices, and materials similar or equivalent to those described herein can be used in the practice or testing of the presently-disclosed subject matter, representative methods, devices, and materials are now described.

Following long-standing patent law convention, the terms "a," "an," and "the" refer to "one or more" when used in this application, including the claims. Thus, for example, reference to "a cell" includes a plurality of such cells, and so forth.

Unless otherwise indicated, all numbers expressing quantities of ingredients, properties such as reaction conditions, and so forth used in the specification and claims are to be understood as being modified in all instances by the term "about." Accordingly, unless indicated to the contrary, the numerical parameters set forth in this specification and claims are approximations that can vary depending upon the desired properties sought to be obtained by the presently-disclosed subject matter.

As used herein, the term "about," when referring to a value or to an amount of mass, weight, time, volume, concentration or percentage is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed method.

This invention related to the isolation and use of antibodies as specific inhibitors of fibrin-dependent Pg activation in TPA-induced cerebral hemorrhage and surgical bleeding. More specifically, certain monoclonal antibodies function as inhibitors and act synergistically to reduce plasminogen activation and fibrinolysis with greater potency than plasminogen activator inhibitor-1 (PA1-1). In a model of thromboembolic stroke, these inhibitors significantly reduced brain hemorrhage and surgical bleeding after TPA administration.

In some embodiments of the presently-disclosed invention, a molecule is provided to bind specifically to a human tissue plasminogen activator (TPA) or a TPA mutant to inhibit degradation of human fibrin clots. In some embodiments, the molecule has sub-nanomolar affinity to inhibit fibrin-dependent plasminogen activation with an IC50<5 nM. In some embodiments, the molecule does not affect TPA amidolytic activity or non-fibrin-dependent activation. Yet in some embodiments, the amino acid sequence of said TPA mutant is at least 65% identical to SEQ ID NO: 1 or SEQ ID NO: 2. The TPA mutant may thus also have homologies with these sequences greater than 65%, e.g., 70%, 75%, 80%, 85%, 90%, 95% and so on. A non-limiting of a TPA mutant is reteplase, which is a TPA deletion mutant has 67.7% of the residues found in full length TPA. In some embodiments, the amino acid sequence of the human TPA is SEQ ID NO: 1 or SEQ ID NO: 2. In some embodiments, the molecule is an antibody. Yet in some embodiments, the antibody is a monoclonal antibody.

In some embodiments, the presently-disclosed invention further provides a method for treating systemic bleeding, brain hemorrhage, and/or stroke after TPA treatment in a patient in need of such treatment. The method comprises administering to said patient an effective amount of the molecule, wherein said antibody selectively inhibits fibrin-augmented plasminogen activation in said patient. In some embodiments, the present invention provides a pharmaceutical composition comprises the molecule and a pharmaceutically acceptable carrier.

TPA-induced brain and systemic bleeding in vivo is blocked by potent synergistic inhibitors of TPA's fibrin-dependent plasminogen activation. This implies that hemorrhage is related to TPA's fibrin-targeted mechanism of plasminogen activation and that targeted inhibitors of this process may serve as specific antidotes for TP associated hemorrhage. TPA therapy is beneficial in ischemic stroke and myocardial infarction, but in some patients it is complicated by serious or fatal bleeding in the brain and at other sites. Fear of TPA-induced bleeding has limited the therapeutic use of TPA. In humans, TPA-induced hemorrhage and adverse outcomes are more frequent after prolonged ischemia. Similarly, in experimental stroke, after prolonged ischemia, TPA reproducibly causes brain hemorrhage, breakdown of the blood brain barrier and enhanced neuronal cell death. In non-thrombotic models of stroke there is evidence that TPA may exert toxic effects through mechanisms, such as PDGF-cc cleavage, etc. that do not require plasminogen activation or affect fibrinolytic activity. (See Su E J, Fredriksson L, Geyer M, et al. Activation of PDGF-CC by tissue plasminogen activator impairs blood-brain barrier integrity during ischemic stroke. Nat Med. 2008; 14:731-737.) Under pathological conditions like myocardial ischemia and stroke, the fibrinolytic activity of therapeutic TPA is enhanced by increased levels of circulating fibrin fragments (e.g., D-dimer), which may enhance the bleeding process. (See Barber M, Langhorne P, Rumley A, Lowe G D, Stott D J. D-dimer predicts early clinical progression in ischemic stroke: confirmation using routine clinical assays. *Stroke*. 2006; 37: 1113-1115.)

In addition to therapeutic use of TPA, elevated TPA levels have been associated with excessive systemic bleeding. TPA-induced bleeding has been suspected in patients' post-cardiopulmonary bypass. (See Manji R A, Grocott H P, Leake J, et al. Seizures following cardiac surgery: the impact of tranexamic acid and other risk factors. *Can J Anaesth*. 2012; 59:6-13.) In a similar fashion, in disease conditions such as liver failure and transplantation, high levels of circulating TPA have been linked to bleeding. (See Leiper K, Croll A, Booth N A, Moore N R, Sinclair T, Bennett B. Tissue plasminogen activator, plasminogen activator inhibitors, and activator-inhibitor complex in liver disease. *J Clin Pathol*. 1994; 47:214-217). Fibrinolytic inhibitors (e.g., tranexarnic acid, ε-aminocaproic acid, aprotinin, etc.) reduce the risk of transfusion after surgery. (See Bayes-Genis A, Mateo J, Santalo M, et al. D-Dimer is an early diagnostic marker of coronary ischemia in patients with chest pain. *Am Heart J*. 2000; 140:379-384). However, these agents have broad inhibitory effects on other pathways and associated toxicities. For example, tranexamic acid increases seizures risk after cardiac surgery. (See Manji R A, Grocott H P, Leake J, et al. Seizures following cardiac surgery: the impact of tranexamic acid and other risk factors. *Can J Anaesth*. 2012; 59:6-13). Broad inhibition of fibrinolysis may carry a risk of subsequent thrombotic episodes such stroke, thromboembolism. (See Fergusson D A, Hebert P C, Mazer C D, et al. A comparison of aprotinin and lysine analogues in high-risk cardiac surgery. *N Engl J Med*. 2008; 358:2319-2331). This concern was magnified by the unexpected finding that aprotinin use increased mortality following cardiac surgery. (See Fergusson D A, Hebert P C, Mazer C D, et al. A comparison of aprotinin and lysine analogues in high-risk cardiac surgery. *N Engl J Med*. 2008; 358:2319-2331).

The use of anti-fibrinolytic agents for treating TPA-induced hemorrhage is still very limited, possibly because these agents are known to interfere with other biochemical pathways. PAI-1 or PAI-1 mutants have been shown to suppress TPA-induced bleeding after injury. However, in addition to inhibiting TPA, PAI-1 inhibits uPA, and several other proteases. Through its non-proteinase interactions with vitronectin, heparin, members of the low-density lipoprotein-receptor family and other molecules, PAI-1 has 'pleiotropic' effects on numerous other biological processes and has been implicated in the pathophysiology of several disease processes. Thus PAI-1 has roles in angiogenesis, apoptosis, cell migration and cancer that involve both inhibitory and non-inhibitory functions.

It is an object of the present invention to produce a molecule specific for the TPA with sub-nanomolar dissociation constant (for a review on the definitions and measurements of antibody-antigen affinity, see Neri et al. (1996). Trends in Biotechnol. 14, 465-470).

The term "mutant" as used herein includes peptide with a sequence substantially similar to the sequence of TPA. It is known in the art that a substantially similar amino acid sequence to a reference peptide may yield a mutant peptide with no substantial change in physiological, chemical, or functional properties compared to the reference peptide. In such a case, the reference and mutant peptides would be considered "substantially identical" polypeptides. Sequence identity is used to evaluate the similarity of two sequences; it is determined by calculating the percent of residues that are the same when the two sequences are aligned for maximum correspondence between residue positions. Any known method may be used to calculate sequence identity; for example, computer software is available to calculate sequence identity. Without wishing to be limiting, sequence identity can be calculated by software such as BLAST-P, BLAST-N, or FASTA-N, or any other appropriate software that is known in the art. The substantially identical sequences of the present invention may be at least 65% identical. In another example, the substantially identical sequences may be at least 65, 70, 75, 80, 85, 90, 95, or 100% identical at the amino acid level to sequences described herein.

The term "antibody" (Ab) as used herein includes monoclonal antibodies, polyclonal antibodies, multispecific antibodies and antibody fragments, as long as they exhibit the desired biological activity. The term "monoclonal antibody" as used herein refers to an antibody obtained from a population of substantially homogeneous antibodies, i.e., the individual antibodies that make up the population are identical except for possible naturally occurring mutations. Monoclonal antibodies are highly specific, being directed against a single antigenic site. For example, the monoclonal antibodies useful in the present invention may be prepared by the hybridoma methodology described by Kohler et al., Nature, 256:495 (1975), or may be made using recombinant DNA methods in bacterial, eukaryotic animal or plant cells (see, e.g., U.S. Pat. No. 4,816,567). Additionally, the "monoclonal antibodies" may also be isolated from phage antibody libraries using the techniques described in Clackson et al., Nature, 352:624-628 (1991) and Marks et al., J. Mol. Biol., 222:581-597 (1991), for example.

The monoclonal antibodies herein include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (see U.S. Pat. No. 4,816,567; and Morrison et al., Proc. Natl. Acad. Sci. USA, 81:6851-6855 (1984)).

The term "antibody" (Ab) as used herein also includes antibody fragments. An "antibody fragment" is a portion of an intact antibody, preferably the antigen binding or variable region of the intact antibody. Examples of antibody fragments include but are not limited to: Fab, Fab', F(ab')2, and Fv fragments; diabodies; linear antibodies (see U.S. Pat. No. 5,641,870, Example 2; Zapata et al., Protein Eng. 8(10): 1057-1062 [1995]); single-chain antibody molecules; and multispecific antibodies formed from antibody fragments.

In some embodiments of the present invention, a purified or isolated antibody is provided. The antibody specifically binds to tissue plasminogen activator (TPA) and inhibits tPA-induced fibrinolysis of human clots. In some embodiments, the antibody is a monoclonal antibody. In some embodiments, the antibody is an antibody binding fragment, a chimeric antibody, a bi-specific antibody, a human antibody or humanized antibody. Non-limiting examples of the monoclonal antibody include TPAi-14 and TPAi-23. Both TPAi-14 and TPAi-23 selectively inhibit fibrin-augmented plasminogen activation. The antibody TPAi-14 and TPAi-23 bind to different epitopes of the tPA. In some embodiments, the present invention provides a pharmaceutical composition. The composition includes an effective amount of the antibody that is capable of treating systematic bleeding, brain hemorrhage, and/or stroke, and a pharmaceutically acceptable carrier.

An "purified or isolated antibody" is one which has been identified and separated and/or recovered from a component of its natural environment. Contaminant components of its natural environment are materials which would interfere with diagnostic or therapeutic uses for the antibody, and may include enzymes, hormones, and other proteinaceous or nonproteinaceous solutes. Preferably, the antibody will be purified (1) to greater than 95% by weight of antibody as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or non-reducing conditions using Coomassie blue or, preferably, silver stain. Isolated antibody includes the antibody in situ within recombinant cells since at least one component of the antibody's natural environment will not be present.

Further provided, in some embodiments of the present invention, is a purified or isolated antibody that binds specifically to a human tissue plasminogen activator (TPA) or a TPA mutant to inhibit degradation of human fibrin clots. In some embodiments, the antibody has sub-nanomolar affinity to inhibit fibrin-dependent plasminogen activation with an IC50<5 nM. In some embodiments, the antibody does not affect TPA amidolytic activity or non-fibrin-dependent activation. In some embodiments, the amino acid sequence of the TPA mutant is at least 65% identical to SEQ ID NO: 1 or SEQ ID NO: 2. In some embodiments, the antibody is a monoclonal antibody.

Further still, in some embodiments, the present invention provides a method for treating systemic bleeding, brain hemorrhage and/or stroke after TPA treatment in a patient in need of such treatment, which comprises administering to said patient an effective amount of the antibody, wherein said antibody selectively inhibits fibrin-augmented plasminogen activation in said patient. In some embodiments of the present invention, a pharmaceutical composition is provided. The pharmaceutical composition comprises the antibody and a pharmaceutically acceptable carrier.

In some embodiments, the present invention provides a kit for the treatment of systemic hemorrhage after TPA treatment in a subject in need thereof. The kit comprises a purified or isolated antibody that specifically binds to TPA to inhibit TPA-induced fibrinolysis of human clots and instructions for using said antibody to treat the systemic bleeding, brain hemorrhage and/or stroke.

Further provided, in some embodiments of the present invention, is a method for treating systemic bleeding, brain hemorrhage and/or stroke after tPA treatment in a patient in need of such treatment. The method comprises administering to said patient an effective amount of at least one purified or isolated antibody capable of binding to an epitope of TPA, wherein said antibody selectively inhibits fibrin-augmented plasminogen activation in said patient. In some embodiments, the antibody is selected from the group consisting of a human antibody, a mouse antibody, and a monoclonal antibody. Yet in some other embodiments, the antibody is an antibody binding fragment, a chimeric antibody, a bi-specific antibody, or a human antibody or humanized antibody. Non-limiting examples of the conditions of patient that in need of TPA treatment are ischemic stroke, and acute myocardial infarction. In some embodiments, the antibody reduces tPA-induced cerebral hemorrhage and surgical bleeding. In some embodiments, the antibody inhibits fibrinolysis induced by tPA. In some embodiments, the antibody inhibits the initiation of fibrinolysis. In some embodiments, the antibody inhibits fibrinolysis in progress. In some embodiments, the antibody reduces brain hemorrhage, surgical bleeding and brain cell death. Non-limiting examples of the at least one purified or isolated antibody is identified as TPAi-14 and TPAi-23. Both TPAi-14 and TPAi-23 selectively inhibit fibrin-augmented plasminogen activation, and both TPAi-14 and TPAi-23 bind with high affinity to different epitopes on tPA. In some embodiments, TPAi-14 and TPAi23 are used together and synergistically inhibit fibrinolysis induced by tPA.

The compositions of the invention may include an "effective amount" or "therapeutically effective amount" or a "prophylactically effective amount" of an antibody or antigen-binding portion of the invention. these terms are used interchangeably. A "therapeutically effective amount" refers to an amount effective, at dosages and for periods of time necessary, to achieve the desired therapeutic result. A therapeutically effective amount of the antibody or antibody portion may vary according to factors such as the disease state, age, sex, and weight of the subject, and the ability of the antibody or antibody portion to elicit a desired response in the subject. Dosage unit form as used herein refers to physically discrete units suited as unitary dosages for the mammalian subjects to be treated; each unit containing a predetermined quantity of active compound calculated to produce the desired therapeutic effect in association with the required pharmaceutical carrier.

In some embodiments, the present invention relates to compositions made of antibodies and/or antigen-binding fragments thereof that are capable of inhibiting TPA-induced fibrinolysis for the treatment of subjects in need of a therapeutic procedure. In some embodiments, the subject of treatment is a human. In other embodiments, the subject is a veterinary subject. Treatment may involve administration of one or more, antibodies and/or antigen-binding fragments that are capable of inhibiting TPA-induced fibrinolysis alone or with a pharmaceutically acceptable carrier.

Further provided, in some embodiments in the presently-disclosed invention, is a method for identifying molecules that can inhibit TPA-induced fibrinolysis of human clots. The method includes the following steps: providing a monoclonal antibody that specifically binds to TPA and inhibits TPA-induced fibrinolysis of human clots, affixing said monoclonal antibody to a surface, providing TPA and introducing an agent to said tPA that blocks the non-specific binding regions of TPA, introducing a candidate molecule to said TPA, introducing said TPA to said monoclonal antibody, determining if said candidate molecule has bound to the epitope of the TPA where said monoclonal antibody had bound to the TPA, and identifying any candidate molecule binding to said epitope as a molecule that can inhibit TPA-induced fibrinolysis of human clots. Non-limiting examples of the monoclonal antibody include TPAi-14 and TPAi-23. In one example of the embodiment, TPAi-14 is immobilized in the wells of a microtiter plate. Non-specific protein binding sites are blocked. A mixture of TPA and the potential new inhibitor molecule, pre-incubated together are added to the wells containing immobilized TPAi-14. After an hour, wells are washed and polyclonal anti-TPA antibody coupled to peroxidase is added. After an hour wells are washed and the peroxidase substrate TMB is added and the A370 is monitored. Wells with reduced A370 contain molecules that compete with TPAi-14 for TPA binding and are thus prime candidates as specific TPA inhibitors. That will be confirmed in detailed studies of human clot lysis initiated by TPA.

The presently-disclosed subject matter is further illustrated by the following specific but non-limiting example.

EXAMPLE

Inhibitory Effects of TPAi-14 and TPAi-23 are Specific to Fibrinolysis Induced by Human TPA Materials There is currently no specific treatment for TPA-induced hemorrhage once it occurs. There have been a number of experimental strategies developed to prevent brain hemorrhage during TPA therapy. Neuroprotective agents (e.g. free radical scavengers and activated protein C) that inhibit TPA-initiated NF-κB and matrix metalloproteinases signaling pathways, have been shown to reduce TPA-induced brain hemorrhage, but their effects on systemic bleeding are unknown.

In this study, the specific inhibition of TPA's fibrin-dependent Pg activation reduces brain hemorrhage and surgical bleeding. These specific inhibitors also diminished neuronal damage and showed a trend to reduced brain swelling.

By comparison to PAI-1, the inhibitory effect of the mAbs studied was more specific and narrowly restricted. Both TPAi-14 and TPAi-23 selectively inhibit fibrin-augmented Pg activation. However, they did not inhibit the catalytic ability of TPA to activate Pg in the absence of fibrin, nor did they affect the catalytic activity of TPA with a small peptide substrate. When compared to a mutant recombinant PAI-1 with enhanced stability and inhibitor activity, these mAbs were more potent and specific inhibitors of fibrinolysis induced by TPA but did not affect other Pg activators. The binding affinity of these mAbs also restricts their inhibitory function to pathologically or pharmacologically elevated levels of TPA. That is because by virtue of $K_D$s of 0.1-0.3 nM, they effectively inhibit TPA activity under conditions when TPA concentrations are ≥1 nM, but are weaker inhibitors when TPA levels are physiologic, e.g. below ~0.5 nM.

TPAi-14 and TPAi-23 are monoclonal antibodies that bind with high affinity to different sites in the TPA molecule. In mechanistic studies TPAi-14 and TPAi-23 specifically inhibited TPA's fibrin-dependent, but not fibrin-independent plasminogen activation, nor TPA's catalytic activity with small substrates. TPAi-14 and TPAi-23 interact synergistically to inhibit TPA-induced fibrinolysis of human clots. By comparison to a plasminogen activator inhibitor-1 mutant, TPAi-14 and TPAi-23 inhibited TPA-induced fibrinolysis with greater potency and specificity. When given after the initiation of TPA therapy, TPAi-14 and TPAi-23 reduced brain hemorrhage (5-fold, $p<0.01$) and surgical bleeding (4-fold, $p<0.01$) as well as brain cell death in a murine thromboembolic model that simulates human stroke. Taken together, these data suggest that fibrin-dependent activation of plasminogen by TPA contributes to hemorrhage and adverse outcomes in stroke. Selective inhibitors of this process may prove useful for treating TPA induced hemorrhage.

Materials

Reagents were purchased from the following sources: DMEM high glucose medium, fetal bovine serum, penicillin-streptomycin solution, L-glutamine, goat anti-mouse (H+L) agarose (Invitrogen, Grand Island, N.Y.); human TPA (Genentech, S. San Francisco, Calif.); human urokinase Pg activator (uPA) (Abbott Laboratory, North Chicago, Ill.), recombinant staphylokinase (SAK, ProSpec-Tany Technogene, East Brunswick, N.J.); mouse TPA, stable mutant human PAI-1(four amino acid substitutions, N150H, K 154T, Q319L, and M354I), mouse anti-human PAI-1 antibody MA-33HIF7 (Molecular Innovations, Novi, Mich.); mouse antibody isotyping kit (Zymed Laboratory, San Francisco, Calif.), Glu-Pg, human cyanogen bromide digested fibrinogen, anti-uPA inhibitory antibody 394 (American Diagnostica Inc., Stamford, Conn.); chromogenic substrate for plasmin (H-D-valyl-L-leucyl-L-lysine-p-nitroanilide dihydrochloride S2251) and TPA (H-D-isoleucyl-L-prolyl-L-arginine-p-nitroanilide dihydrochloride, S2288) (Chromogenix Instrumentation Laboratory, Lexington, Mass.); d-Phe-Pro-Arg chloromethylketone (PPACK) (Calbiochem, San Diego, Calif.); citrated frozen human and mouse plasma (Lampire Biological Laboratories, Pipersville, Pa.); 125I-fibrinogen (Perkin-Elmer, Waltham, Mass.); horse radish peroxidase (HRP) conjugated goat antimouse IgG (Santa Cruz Biotechnology, Inc, Santa Cruz, Calif.), 3,3',5,5'-tetramethylbenzidine (TMB) substrate, Pierce Plus activated HRP conjugation kit (Fisher Scientific, Rockfold, Ill.); non-TPA reactive antibody (IgGI). Runge M S, Bode C, Matsueda G R, Haber E. Antibody-enhanced thrombolysis: targeting of tissue plasminogen activator in vivo. Proc Natl Acad Sci USA. 1987; 84:7659-7662. All the other reagents if not specified (Sigma, St. Louis, Mo.).

Monoclonal Antibody Generation

C57BL/6J mice (Jackson Laboratory, Bar Harbor, Me.) were immunized with recombinant human TPA followed by fusion of splenocytes isolated from the immunized mouse with myeloma cells using the conventional hybridoma techniques. Nelson P N, Reynolds G M, Waldron E E, Ward E, Giannopoulos K, Murray P G. Monoclonal antibodies. Mol Pathol. 2000; 53: 111-117. Microplate ELISA assays were performed to screen positive clones as described below. Positive clones were further subcloned by limited dilution to create stable monoclonal antibody (mAb). All cell cultures were maintained in DMEM medium, supplemented with 5% fetal bovine serum, 2 mmol/L L-glutamine, and 1% penicillin-streptomycin in a humidified 5% $CO_2$/95% air incubator at 37° C. Mouse mAb was purified from culture medium with goat anti-mouse lgG agarose and further characterized with mouse antibody isotyping kit.

ELISA Assay for Detecting TPA and Anti-TPA mAb Binding

To screen positive TPA binding clones or to detect TPA and anti-TPA mAb binding, microplates were coated with 1-211 g/ml TPA (human/mouse TPA, or bovine serum albumin (BSA)) in phosphate buffered saline (PBS) for one hour at room temperature, followed by blocking with 1% BSA in PBS for one hour. After that, mouse serum, hybridoma cell culture supernatant, or 2-5 µg/ml purified anti-TPA mAb in PBS solution was loaded and incubated for one hour. The bound mAb was detected by HRP conjugated goat anti-mouse IgG with TMB substrate. In some runs, 3 µg/ml human PAI-1 was incubated in TPA coated BSA blocked wells before the addition of anti-TPA mAb to examine the binding between mAb and TPA-PAI-1 complex; complex formation was confirmed by detection of bound PAI-1 with mouse anti-human PAI-1 mAb. TPA and anti-TPA mAb binding constants were estimated by saturation binding experiment with ELISA assay. Briefly, 7.5 µg/ml purified anti-TPA mAb in PBS were coated on microplate for one hour at room temperature, followed by blocking with 1% BSA in PBS. Varying concentrations of human TPA (0-4 µg/ml) were then loaded in human serum pre-quenched with 20 µM PPACK and 200 kallikrein inhibitor units aprotinin. Bound TPA was detected with HRP-conjugated mouse anti-human TPA polyclonal antibody, followed by TMB substrate. The reaction was monitored at A370 nm within the dynamic range of the microplate reader. Binding constants were calculated using Graphpad Prism Software (La Jolla, Calif.). To test if anti-TPA mAb competes with each other for binding with TPA, 211 g/ml TPA was coated on microplates. After blocking with I% BSA in PBS, varying concentration of HRP-labeled anti-TPA mAb were added. After washing, the bound mAb were detected with TMB substrate. In some wells, varying concentrations of purified anti-TPA mAb was added to a fixed amount of HRP-labeled anti-TPA mAb to compete the binding for coated TPA. The percent inhibition of binding was calculated based on the difference between bound HRP labeled mAb in the absence and presence of purified anti-TPA mAb.

Assays of TPA Activity

The amidolytic activity of TPA was examined with 500 µM chromogenic substrate S2288. Pg activation by TPA was determined by monitoring the amidolytic activity of plasmin with 500 µM S2251. All experiments were performed at 37° C. in Tris-NaCl buffer (50 mM Tris-HCl, 100 mM NaCl, pH 7.4) as described previously. Sazonova I Y, McNamee R A, Houng A K, King S M, Hedstrom L, Reed G L. Reprogrammed streptokinases develop fibrin-targeting and dissolve blood clots with more potency than tissue plasminogen activator. J Thromb Haemost. 2009; 7: 1321-1328. Pg was pretreated with aprotinin-agarose beads for four hours at 4° C. to remove contaminating plasmin. In both assays, the absorbance at 405 nm (A405 nm) was continuously recorded. The amidolytic activity of TPA was determined from the initial slope of A405 nm with time. The activation rate of Pg by TPA to plasmin was calculated using the change in A405 nm per second squared over the initial period of reaction when net change of absorbance was less than 0.1, based on the method described by Longstaff et al. Longstaff C, Whitton C M. A proposed reference method for plasminogen activators that enables calculation of enzyme activities in SI units. J Thromb Haemost. 2004; 2: 1416-1421. In some runs, anti-TPA mAb or fibrin (Fn) fragment was incubated with TPA to examine their effect on TPA activity or Pg activation.

Fibrinolysis

Human clots were formed by mixing 20 µl human plasma (with trace amount of $^{125}$I-fibrinogen) with 5 µl mixture of thrombin and calcium solution (final concentration: 1 Ul/ml thrombin and 10 mM Ca2l in test tube. The clot was incubated at 37° C. for one hour, followed by the addition of total 45 µl of varying amounts of human. TPA, uPA or SAK with or without anti-TPA mAb. At sampling time, 10 µl supernatant was collected and the radioactivity of this sample was monitored using Cobra II gamma counter (Perkin-Elmer-Packard BioScience, Waltham, Mass.). After gamma counting, the samples were replaced in the test tube. The percent fibrinolysis was determined by the radioactivity in the supernatant divided by the initial clot radioactivity. The percent inhibition of fibrinolysis by mAbs was calculated by reference to the amount of fibrinolysis in the absence of mAbs.

Mouse Middle Cerebral Artery Thromboembolic Stroke and Bleeding

Animal studies were approved by the Institutional Animal Care and Use Committee. C57BL/6J adult mice (29 to 35 g, Jackson Lab, Bar Harbor, Me.) were anesthetized with a mixture of 1.5-2% isoflurane and oxygen throughout the study. Rectal temperature was maintained at 3iC with a thermostat controlled heating pad. The left common carotid artery was isolated after a neck incision, and the external carotid, thyroid, and occipital arteries were ligated. Microvascular clips were temporarily placed on the common carotid and internal carotid arteries. A small arteriotomy was made on the external carotid artery for retrograde insertion of the PES catheter containing emboli $^{125}$I-fibrinogen (~5000 cpm/2 µl). The PES tubing containing the clots were inserted into the left external carotid artery, threaded into the internal cerebral artery up to origin of the middle cerebral artery (MCA). The thrombus was embolized at a speed of 0.45 ml/min in a volume of 100 µl saline. Continuous laser-Doppler monitoring was used to assess regional cerebral perfusion to ensure adequacy of embolization (perfusion decreased to <20% of preischemic base line). The right jugular vein was cannulated for drug administration. Mice received TPA (10 mg/kg at 2.5 hr of ischemia) as a 20% bolus, SO % infusion over 30 minutes. Mice receiving mAb inhibitors were treated by stoichiometric dose of TPAi-14 and TPA-23 given as an intravenous bolus after the TPA bolus. Tail bleeding was assessed 20 mins. after the TPA infusion and monitored for 30 mins by measuring the time and amount of bleeding from tails pre-warmed for 5 mins in 3 mL of saline at 37° C. in a water bath as described. Hemoglobin (Hgb) loss from tail bleeding was measured using Drabkin's reagent kit according to manufacturer's data sheet (Sigma, St. Louis, Mo.). Six hours after thromboembolism, the brain was isolated, cut into 2-mm coronal section, and incubated in 2% triphenyltetrazolium chloride (Sigma, St. Louis, Mo.) solution for 30 mins at room temperature. The stained slices then were transferred into 4% formaldehyde for fixation. Images of four brain sections were captured with digital camera. The hemispheric size, area of gross hemorrhage and infarction area were digitally analyzed using Image Pro Plus 6.2 software and a modified Swanson's method. Swanson R A, Morton M T, Tsao-Wu G, Savalos R A, Davidson C, Sharp F R. A semiautomated method for measuring brain infarct volume. J Cereb Blood Flow Metab. 1990; 10:290-293. The amount of clot lysis was determined by comparing the residual thrombus radioactivity in the brain to that of the initial clot.

Statistical Analysis

The results are expressed as the mean±SD. Comparisons between two groups were analyzed by two tailed t tests. Differences of p≤0.05 were considered significant.

Figure 1:
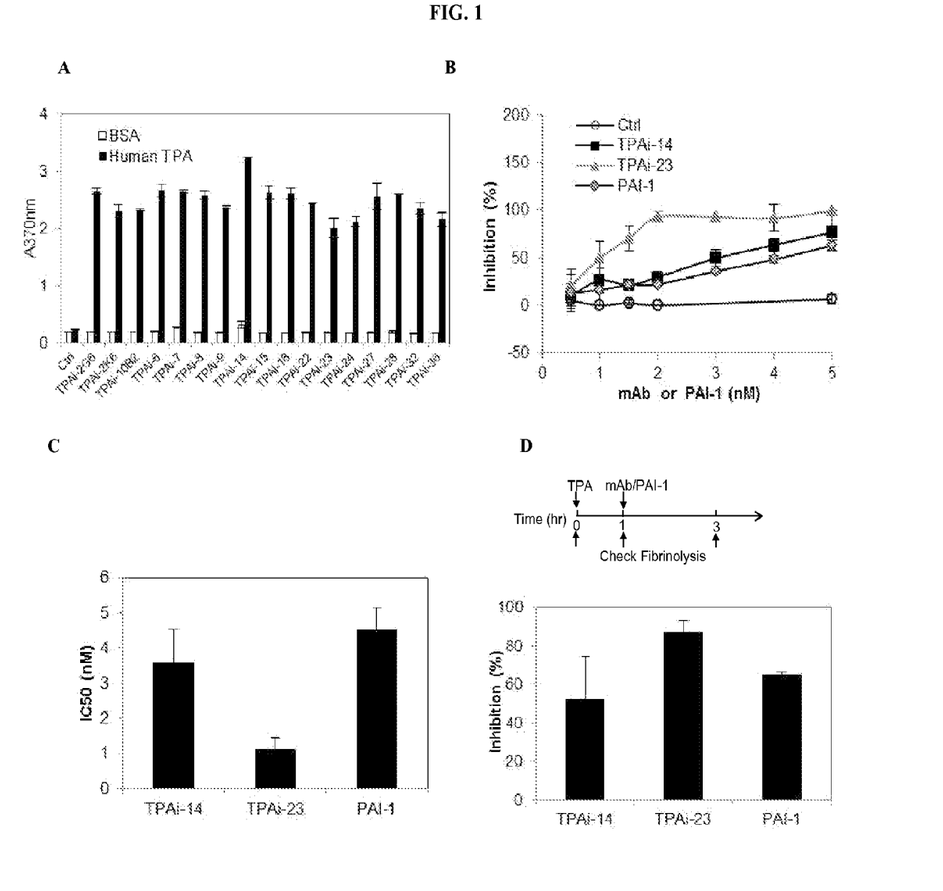

Now referring to FIG. 1, seventeen hybridomas produced mAbs that bound specifically to TPA in an ELISA (FIG. 1A). Two of these mAbs, TPAi-14 and TPAi-23, inhibited TPA-induced fibrinolysis in screening assays. By comparison to a control (non-reactive) mAb, TPAi-14 and TPAi-23 inhibited fibrinolysis in a dose dependent manner (FIG. 1B). TPAi-23 inhibited fibrinolysis by 50% at 1 nM concentrations (IC50=1.12 nM, 95% confidence interval (CI)=0.88-1.44 nM, FIG. 1C) and nearly 100% at 2 nM concentration. TPAi-14 was less potent and achieved 50% inhibition at a concentration of 3 nM (IC50=3.59 nM, 95% C12.85-4.54 nM, FIG. 1C). The inhibitory potency of TPAi-14 and TPAi-23 were compared with a stable mutant form of PAI-1. Yang D, Nemkul N, Shereen A, et al. Therapeutic administration of plasminogen activator inhibitor-1 prevents hypoxic-ischemic brain injury in newborns. J Neurosci. 2009; 29:8669-8674. Approximately 4 nM PAI-1 was required to inhibit 50% of the clot lysis ([C50=4.53 nM, 95% CI=3.99-5.14 nM, FIGS. 1B and 1C).

In addition to inhibiting the initiation of fibrinolysis, TPAi-14 or TPAi-23 also inhibited fibrinolysis in progress. When added 1 hr. after the initiation of fibrinolysis, TPAi-14 inhibited subsequent fibrinolysis by 52±22%, TPAi-23 inhibited by 87±6% and the stabilized PAI-1 mutant inhibited lysis by 66±1% during the subsequent two hrs.

Figure 2:
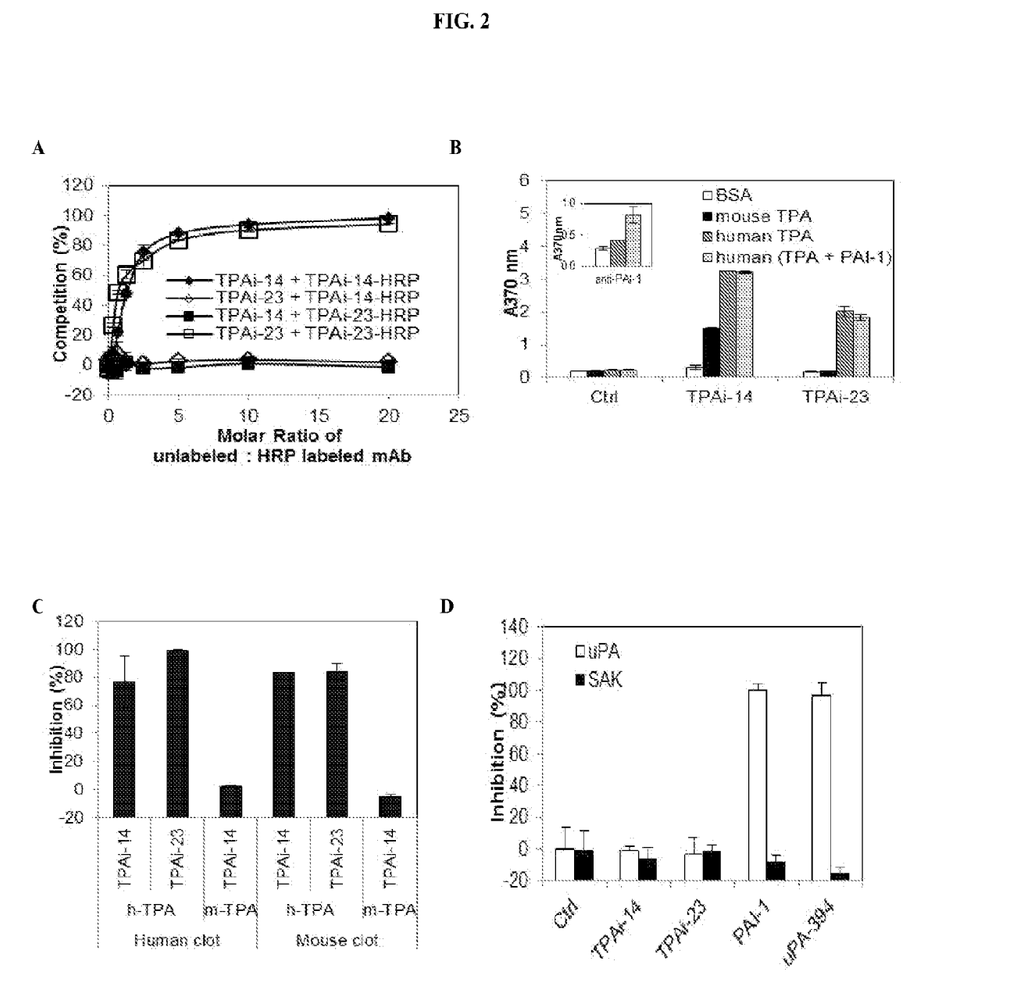

TPAi-14 and TPAi-23 displayed high binding affinity to human TPA (Kn=257±70 pM and 134±23 pM, respectively). Neither TPAi-14 nor TPAi-23 competed with each other for binding for human TPA suggesting they recognized a different epitope (FIG. 2A). Both TPAi-14 and TPAi-23 bound equivalently to human TPA and TPA-PAI-1 complex, indicating that the mAb binding sites on human TPA do not compete with its PAI-1 binding site (FIG. 2B).

TPAi-14 bound to mouse TPA but TPAi-23 did not (FIG. 2B). However, TPAi-14 did not affect fibrinolysis induced by mouse TPA, either in a human or mouse plasma clot; both TPAi-14 and TPAi-23 inhibited the fibrinolysis of mouse plasma clots initiated by human TPA (FIG. 2C). Hence, these two mAbs specifically inhibited human but not mouse TPA. In a similar fashion, neither TPAi-14 nor TPAi-23 inhibited fibrinolysis induced by low molecular weight uPA, the other endogenous Pg activator with important physiological roles. In contrast, PAI-1 potently inhibited fibrinolysis initiated by uPA (FIG. 2D). In addition, TPAi-14 or TPAi-23 did not affect fibrinolysis triggered by staphylokinase an indirect plasminogen activator that forms a complex with plasmin (FIG. 2D).

Effects of TPAi-14 and TPAi-23 on Catalytic Activity of TPA

Figure 3:
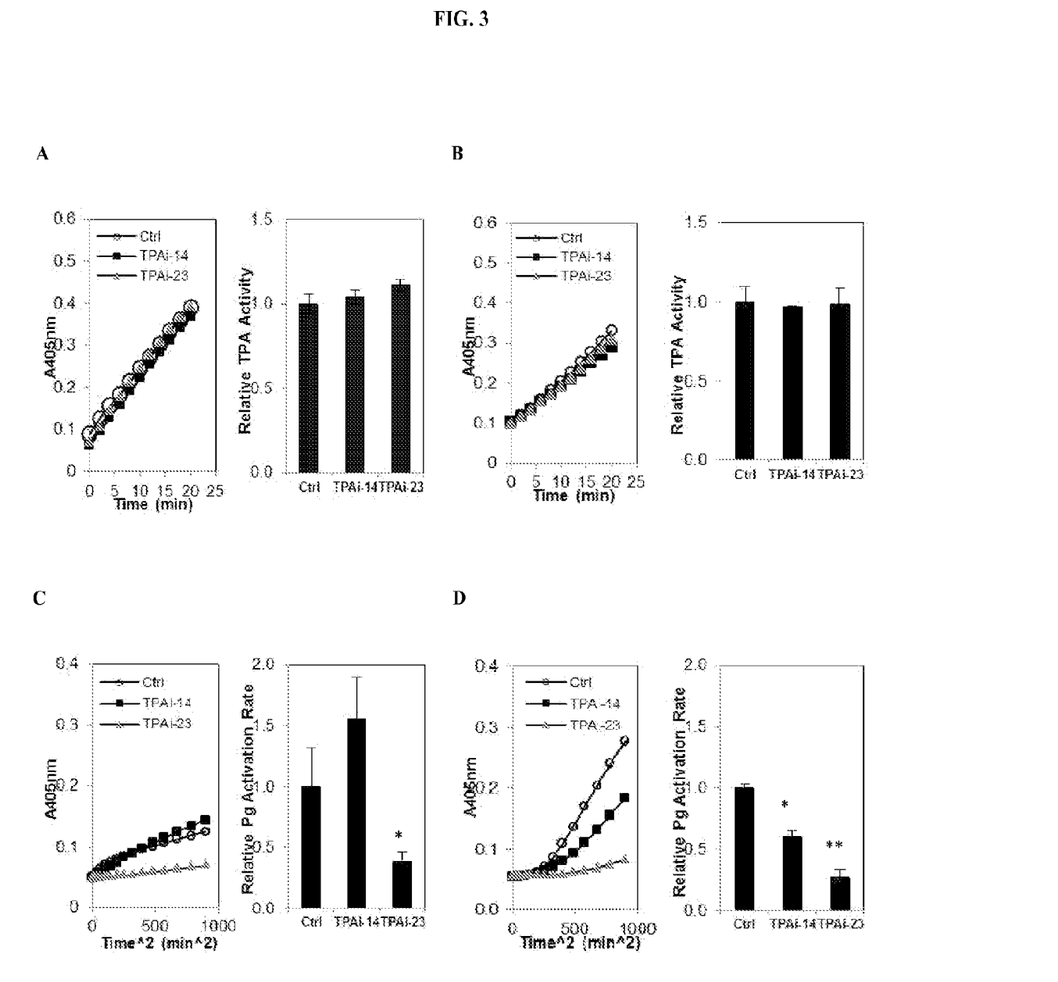

The finding that TPAi-14 and TPAi-23 inhibited fibrinolysis by TPA, but not other plasminogen activators, suggests that it specifically interfered with TPA-induced plasminogen activation or catalytic function. To test for a direct effect on catalytic function, we examined if the mAbs affected the amidolytic ability of TPA to cleave a small tripeptide substrate S-2288 in the absence or the presence of cyanogen bromide digested fibrin fragments, which amplify TPA activity. Neither TPAi-14 nor TPAi-23, even in ten molar excess to TPA, affected TPA amidolytic activity. (FIG. 3A). Similarly, TPAi-14 and TPAi-23 did not affect TPA amidolytic activity in the presence of fibrin (FIG. 3B).

Although neither TPAi-14 nor TPAi-23 affected TPA amidolytic activity with a small peptide substrate, they may affect the cleavage activation of Pg by TPA. In the absence of TPA neither mAb itself affected the spontaneous activation of Pg (data not shown). Interestingly, when 100 nM Pg was activated with 20 nM human TPA, TPAi-14 slightly accelerated Pg activation; in contrast, TPAi-23 reduced the Pg activation rate compared to non-reactive mAb control (FIG. 3C). However, in the presence of fibrin, which significantly amplifies Pg activation, both TPAi-23 and TPAi-14 inhibited TPA induced Pg activation (FIG. 3D), in a dose-dependent fashion (data not shown). Taken together, these results indicate that both TPAi-14 and TPAi-23 exert their primary inhibitory effects by interfering with fibrin dependent Pg activation by TPA.

Figure 4:
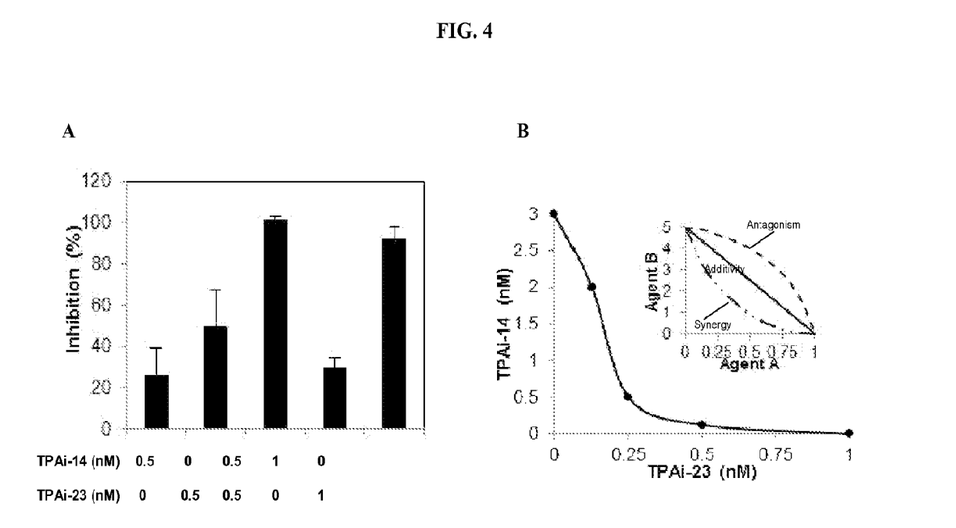

TPAi-14 and TPAi-23 Interact Synergistically to Neutralize TPA-induced Fibrinolysis Competitive binding studies indicated that TPAi-14 and TPAi-23 bound to different sites on the TPA molecule (FIG. 2A) and exerted different effects on TPA-induced Pg activation (FIGS. 3C and 3D). Using established pharmacologic criteria, we examined whether these two agents may interact in an additive, antagonistic or synergistic fashion to affect TPA-induced fibrinolysis. Berenbaum M C. The expected effect of a combination of agents: the general solution. J Theor Bioi. 1985; 114:413-431. When compared to equimolar doses of each antibody alone, the combination of 0.5 nM TPAi-14 and 0.5 nM TPAi-23 had greater inhibitory effect than equivalent amounts (I nM) of each individual mAb (FIG. 4A). To illustrate this more clearly, an isobologram, Berenbaum M C. The expected effect of a combination of agents: the general solution. J Theor Bioi. 1985; 114:413-431, was constructed that shows the equivalent levels of inhibition of TPA-induced fibrinolytic activity for TPAi-14 and TPAi-23 alone or in combination (FIG. 4B). TPAi-14 (3 nM) and TPAi-23 (1 nM) alone were equally potent at achieving 50% fibrinolysis inhibition. However, as shown in FIG. 4B, smaller doses of these two mAbs in combination produced equivalent or more fibrinolysis inhibition than the larger doses of each individual mAb alone, confirming that TPAi-14 and TPAi-23 interact synergistically to inhibit TPA.

Figure 5:
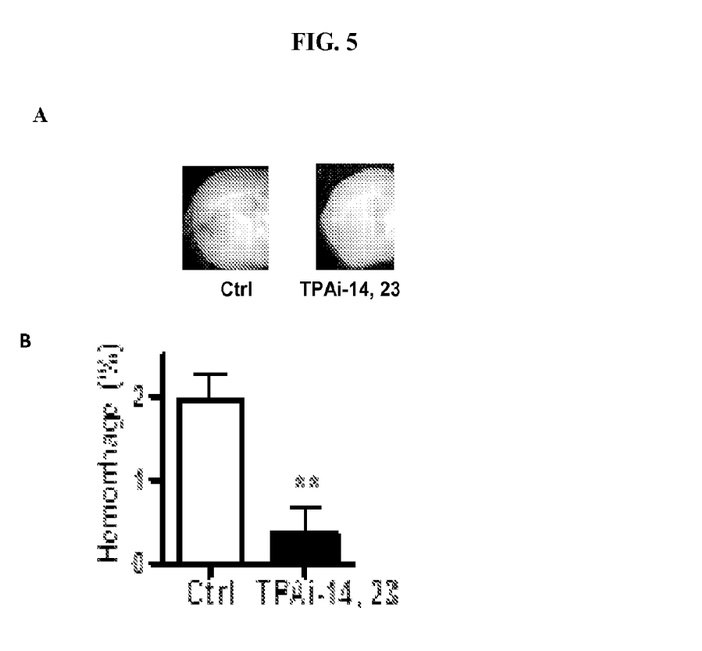
FIG. 5 includes images and graphs showing the inhibition of fibrin-dependent plasminogen activation reduces cerebral hemorrhage, surgical bleeding and infarction after TPA treatment for stroke. Ischemic stroke was induced by MCA thromboembolism. After 2.5 hrs. mice were treated with a standard dose of TPA followed by equimolar dose of TPAi-14 and TPAi-23 (n=5) or nothing (control, n=5). Tail bleeding was assessed during TPA infusion. Six hours after embolism, anesthetized mice were euthanized, perfused and the brain was harvested for examination for hemorrhage and infarction as described in Methods. A) Images of hemorrhages in mouse brain tissue sections from the control group and the treatment group. B) The total percentage of brain hemorrhage. C) Area infarction as percent of brain. D) Tail bleeding time. E) Total hemoglobin (Hgb) loss from tail bleeding. $p<0.01$, *$p<0.001$, ****$p<0.0001$ vs. control.

Inactivation of TPA-Induced Pg Activation Reduces Brain Hemorrhage and Bleeding after TPA Treatment for Ischemic Stroke TPA-induced brain hemorrhage and bleeding are serious complications of TPA therapy for ischemic stroke. In a thromboembolic model that simulates severe, middle cerebral artery stroke, TPA induced brain hemorrhage when given 2.5 hrs. after the onset of ischemia (FIG. 5A). When given as a synergistic combination after the onset of TPA therapy, TPAi-14 and TPAi-23 reduced brain hemorrhage by more than 5-fold (2.0+0.7% vs. 0.4+0.6%, p<0.01, FIGS. 5A and 5B). There was no reduction in fibrinolysis already initiated by TPA administration (55.1±1.1% vs. 56.1±2.6%, p=0.453). However, there was a marked reduction in stroke infarct size consistent with a decrease in TPA-induced neurotoxicity (52.5±5.6% vs. 27.3±6.6%, p<0.001, FIG. 5C). There was a trend to reduced brain swelling (12.7±5.4% vs. 7.2±1.7%, p=0.062). Administration of the mAbs after TPA treatment also reduced surgical tail bleeding; tail bleeding time in control group dropped from 25.7±1.3 min to 6.5±5.1 min in mAb treated group (p<0.0001, FIG. 5D). There was also a marked reduction in total blood hemoglobin loss (6.4±2.7 mg vs. 1.6±1.5 mg, p<0.01, FIG. 5E). Thus specific inactivation of TPA after TPA treatment significantly reduced brain hemorrhage and tail bleeding.

Whether specific inhibitors of TPA's fibrin-dependent activation of plasminogen could reduce bleeding after the initiation of TPA therapy for ischemic stroke is examined Hybridomas were screened for the production of monoclonal antibodies (MAbs) that inhibited TPA-induced fibrinolysis. After molecular characterization and purification, these MAbs were tested for their ability to stop brain hemorrhage and systemic bleeding triggered by TPA therapy for ischemic stroke.

RESULTS: Two MAbs were selected that bound with high affinity (subnanomolar dissociation constants) to different epitopes on the TPA molecule. These MAbs preferentially inhibited TPA's fibrin-dependent plasminogen activation but not other catalytic functions; they did not affect plasminogen activation by other agents. When added to human clots, these MAbs synergistically blocked TPA fibrinolysis with greater specificity and potency than a stabilized form of plasminogen activator inhibitor 1. When administered after the onset of TPA therapy for ischemic stroke, these MAbs significantly reduced brain hemorrhage (p<0.05) but did not worsen infarction. The MAbs also markedly diminished TPA-triggered tail bleeding and hemoglobin loss in anesthetized mice.

CONCLUSION

This study shows that specific inhibition of TPA's fibrin-dependent Pg activation reduces brain hemorrhage and surgical bleeding. These specific inhibitors also diminished neutonal damage (brain infarction) and showed a trend to reduced brain swelling. The present study provides a demonstration that specific inhibition of TPA's fibrin-dependent mechanism of Pg activation reduces brain hemorrhage, infarction and surgical bleeding in thromboembolic ischemic stroke after TPA has been given. This suggests that fibrin-dependent plasminogen activation per se contributes to these adverse outcomes. An agent that selectively inhibits this process to treat TPA-induced hemorrhage may help to promote wider use of TPA in patients who are likely to benefit from treatment.

All publications, patents and patent applications herein are incorporated by reference to the same extent as if each individual publication or patent application was specifically and individually indicated to be incorporated by reference. The foregoing detailed description has been given for clearness of understanding only and no unnecessary limitations should be understood therefrom as modifications will be obvious to those skilled in the art. It is not an admission that any of the information provided herein is prior art or relevant to the presently claimed inventions, or that any publication specifically or implicitly referenced is prior art. Unless defined otherwise, all technical and scientific terms used herein have the same meaning as commonly understood by one of ordinary skill in the art to which this invention belongs.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth and as follows in the scope of the appended claims.

SEQUENCES

```
SEQ ID NO: 1. GenBank ® Accession No. AAA01378.1.
  1 mdamkrglcc vlllcgavfv spsqeiharf rrgarsyqvi crdektqmiy qqhqswlrpv 61 lrsnrveycw cnsgraqchs vpvkscsepr cfnggtcqqa lyfsdfvcqc pegfagkcce 121 idtratcyed qgisyrgtws taesgaectn wnssalaqkp ysgrrpdair lglgnhnycr 181 npdrdskpwc yvfkagkyss efcsTPAcse gnsdcyfgng sayrgthslt esgasclpwn
```

-continued

```
241 smiligkvyt aqnpsaqalg lgkhnycrnp dgdakpwchv lknrrltwey cdvpscstcg 301 lrqysqpqfr ikgglfadia shpwqaaifa khrrspgerf lcggilissc wilsaahcfq 361 erfpphhltv ilgrtyrvvp geeeqkfeve kyivhkefdd dtyndiall qlksdssrca 421 qessvvrtvc lppadlqlpd wtecelsgyg khealspfys erlkeahvrl ypssrctsqh 481 llnrtvtdnm lcagdtrsgg pqanlhdacq gdsggplvcl ndgrmtlvgi iswglgcgqk 541 dvpgvytkvt nyldwirdnm rp SEQ ID NO: 2. GenBank ® Accession No. AAA01895.1.
  1 mdamkrglcc vlllcgavfv spsqeiharf rrgarsyqvi crdektqmiy qqhqswlrpv 61 lrsnrveycw cnsgraqchs vpvkscsepr cfnggtcqqa lyfsdfvcqc pegfagkcce 121 idtratcyed qgisyrgtws taesgaectn wnssalaqkp ysgrrpdair lglgnhnycr 181 npdrdskpwc yvfkagkyss efcsTPAcse gnsdcyfgng sayrgthslt esgasclpwn 241 smiligkvyt aqnpsaqalg lgkhnycrnp dgdakpwchv lknrrltwey cdvpscstcg 301 lrqysqpqfr ikgglfadia shpwqaaifa khrrspgerf lcggilissc wilsaahcfq 361 erfpphhltv ilgrtyrvvp geeeqkfeve kyivhkefdd dtyndiall qlksdssrca 421 qessvvrtvc lppadlqlpd wtecelsgyg khealspfys erlkeahvrl ypssrctsqh 481 llnrtvtdnm lcagdtrsgg pqanlhdacq gdsggplvcl ndgrmtlvgi iswglgcgqk 541 dvpgvytkvt nyldwirdnm rp
```

---

What is claimed is:

1. An antibody that binds specifically to a human tissue plasminogen activator (TPA) or a TPA mutant to inhibit degradation of human fibrin clots, wherein said antibody having sub-nanomolar affinity to inhibit fibrin-dependent plasminogen activation with an IC50<5 nM, and wherein the amino acid sequence of said TPA mutant has at least 65% identity to SEQ ID NO: 1 or SEQ ID NO: 2; and wherein said antibody is a monoclonal antibody identified as TPAi-14 (ECACC accession number 18042001) or TPAi-23 (ECACC accession number 18042002) that selectively inhibits fibrin-augmented plasminogen activation.

2. The antibody of claim 1, wherein the antibody does not affect TPA amidolytic activity or non-fibrin-dependent activation.

3. The antibody of claim 1 wherein the amino acid sequence of human TPA is SEQ ID NO: 1 or SEQ ID NO: 2.

4. The antibody of claim 1, wherein monoclonal antibody TPAi-14 and TPAi-23 bind to different epitopes of the TPA.

5. A monoclonal antibody identified as TPAi-14 (ECACC accession number 18042001) or TPAi-23 (ECACC accession number 18042002) that selectively inhibits fibrin-augmented plasminogen activation.

6. A method for treating TPA-induced hemorrhage in a patient in need of such treatment, which comprises administering to said patient an effective amount of the antibody of claim 1, wherein said antibody selectively inhibits fibrin-augmented plasminogen activation in said patient.

7. The method of claim 6, wherein the patient suffers from ischemic stroke.

8. The method of claim 6, wherein the patient suffers from acute myocardial infarction.

9. The method of claim 6, wherein the antibody reduces TPA-induced cerebral hemorrhage and surgical bleeding.

10. The method of claim 6, wherein the antibody inhibits fibrinolysis induced by TPA.

11. The method of claim 10, wherein said antibody inhibits the initiation of fibrinolysis.

12. The method of claim 6, wherein said antibody is identified as TPAi-14.

13. The method of claim 6, wherein said antibody is identified as TPAi-23.

14. The method of claim 6, wherein TPAi-14 and TPAi23 are used together and synergistically inhibit fibrinolysis induced by TPA.

15. The method of claim 6, wherein the TPA-induced hemorrhage comprises systemic bleeding, brain hemorrhage, and/or stroke.

* * * * *

SEQUENCE LISTING

<160> NUMBER OF SEQ ID NOS: 2

<210> SEQ ID NO 1
<211> LENGTH: 562
<212> TYPE: PRT
<213> ORGANISM: unknown
<220> FEATURE:
<223> OTHER INFORMATION: recombinant human TPA

<400> SEQUENCE: 1

```
Met Asp Ala Met Lys Arg Gly Leu Cys Cys Val Leu Leu Cys Gly
1               5                   10                  15

Ala Val Phe Val Ser Pro Ser Gln Glu Ile His Ala Arg Phe Arg
                20                  25                  30

Gly Ala Arg Ser Tyr Gln Val Ile Cys Arg Asp Glu Lys Thr Gln Met
                35                  40                  45

Ile Tyr Gln Gln His Gln Ser Trp Leu Arg Pro Val Leu Arg Ser Asn
    50                  55                  60

Arg Val Glu Tyr Cys Trp Cys Asn Ser Gly Arg Ala Gln Cys His Ser
65                  70                  75                  80

Val Pro Val Lys Ser Cys Ser Glu Pro Arg Cys Phe Asn Gly Gly Thr
                85                  90                  95

Cys Gln Gln Ala Leu Tyr Phe Ser Asp Phe Val Cys Gln Cys Pro Glu
                100                 105                 110

Gly Phe Ala Gly Lys Cys Cys Glu Ile Asp Thr Arg Ala Thr Cys Tyr
            115                 120                 125

Glu Asp Gln Gly Ile Ser Tyr Arg Gly Thr Trp Ser Thr Ala Glu Ser
        130                 135                 140

Gly Ala Glu Cys Thr Asn Trp Asn Ser Ser Ala Leu Ala Gln Lys Pro
145                 150                 155                 160
```

-continued

Tyr Ser Gly Arg Arg Pro Asp Ala Ile Arg Leu Gly Leu Gly Asn His
            165                 170                 175
Asn Tyr Cys Arg Asn Pro Asp Arg Asp Ser Lys Pro Trp Cys Tyr Val
            180                 185                 190
Phe Lys Ala Gly Lys Tyr Ser Ser Glu Phe Cys Ser Thr Pro Ala Cys
            195                 200                 205
Ser Glu Gly Asn Ser Asp Cys Tyr Phe Gly Asn Gly Ser Ala Tyr Arg
        210                 215                 220
Gly Thr His Ser Leu Thr Glu Ser Gly Ala Ser Cys Leu Pro Trp Asn
225                 230                 235                 240
Ser Met Ile Leu Ile Gly Lys Val Tyr Thr Ala Gln Asn Pro Ser Ala
                245                 250                 255
Gln Ala Leu Gly Leu Gly Lys His Asn Tyr Cys Arg Asn Pro Asp Gly
                260                 265                 270
Asp Ala Lys Pro Trp Cys His Val Leu Lys Asn Arg Arg Leu Thr Trp
            275                 280                 285
Glu Tyr Cys Asp Val Pro Ser Cys Ser Thr Cys Gly Leu Arg Gln Tyr
        290                 295                 300
Ser Gln Pro Gln Phe Arg Ile Lys Gly Gly Leu Phe Ala Asp Ile Ala
305                 310                 315                 320
Ser His Pro Trp Gln Ala Ala Ile Phe Ala Lys His Arg Arg Ser Pro
                325                 330                 335
Gly Glu Arg Phe Leu Cys Gly Gly Ile Leu Ile Ser Ser Cys Trp Ile
                340                 345                 350
Leu Ser Ala Ala His Cys Phe Gln Glu Arg Phe Pro Pro His His Leu
            355                 360                 365
Thr Val Ile Leu Gly Arg Thr Tyr Arg Val Val Pro Gly Glu Glu Glu
        370                 375                 380
Gln Lys Phe Glu Val Glu Lys Tyr Ile Val His Lys Glu Phe Asp Asp
385                 390                 395                 400
Asp Thr Tyr Asp Asn Asp Ile Ala Leu Leu Gln Leu Lys Ser Asp Ser
                405                 410                 415
Ser Arg Cys Ala Gln Glu Ser Ser Val Val Arg Thr Val Cys Leu Pro
            420                 425                 430
Pro Ala Asp Leu Gln Leu Pro Asp Trp Thr Glu Cys Glu Leu Ser Gly
            435                 440                 445
Tyr Gly Lys His Glu Ala Leu Ser Pro Phe Tyr Ser Glu Arg Leu Lys
        450                 455                 460
Glu Ala His Val Arg Leu Tyr Pro Ser Ser Arg Cys Thr Ser Gln His
465                 470                 475                 480
Leu Leu Asn Arg Thr Val Thr Asp Asn Met Leu Cys Ala Gly Asp Thr
                485                 490                 495
Arg Ser Gly Gly Pro Gln Ala Asn Leu His Asp Ala Cys Gln Gly Asp
            500                 505                 510
Ser Gly Gly Pro Leu Val Cys Leu Asn Asp Gly Arg Met Thr Leu Val
        515                 520                 525
Gly Ile Ile Ser Trp Gly Leu Gly Cys Gly Gln Lys Asp Val Pro Gly
        530                 535                 540
Val Tyr Thr Lys Val Thr Asn Tyr Leu Asp Trp Ile Arg Asp Asn Met
545                 550                 555                 560
Arg Pro

```
<210> SEQ ID NO 2
<211> LENGTH: 562
<212> TYPE: PRT
<213> ORGANISM: unknown
<220> FEATURE:
<223> OTHER INFORMATION: recombinant human TPA

<400> SEQUENCE: 2

Met Asp Ala Met Lys Arg Gly Leu Cys Cys Val Leu Leu Leu Cys Gly
1               5                   10                  15

Ala Val Phe Val Ser Pro Ser Gln Glu Ile His Ala Arg Phe Arg Arg
            20                  25                  30

Gly Ala Arg Ser Tyr Gln Val Ile Cys Arg Asp Glu Lys Thr Gln Met
        35                  40                  45

Ile Tyr Gln Gln His Gln Ser Trp Leu Arg Pro Val Leu Arg Ser Asn
    50                  55                  60

Arg Val Glu Tyr Cys Trp Cys Asn Ser Gly Arg Ala Gln Cys His Ser
65                  70                  75                  80

Val Pro Val Lys Ser Cys Ser Glu Pro Arg Cys Phe Asn Gly Gly Thr
                85                  90                  95

Cys Gln Gln Ala Leu Tyr Phe Ser Asp Phe Val Cys Gln Cys Pro Glu
            100                 105                 110

Gly Phe Ala Gly Lys Cys Cys Glu Ile Asp Thr Arg Ala Thr Cys Tyr
        115                 120                 125

Glu Asp Gln Gly Ile Ser Tyr Arg Gly Thr Trp Ser Thr Ala Glu Ser
    130                 135                 140

Gly Ala Glu Cys Thr Asn Trp Asn Ser Ser Ala Leu Ala Gln Lys Pro
145                 150                 155                 160

Tyr Ser Gly Arg Arg Pro Asp Ala Ile Arg Leu Gly Leu Gly Asn His
                165                 170                 175

Asn Tyr Cys Arg Asn Pro Asp Arg Asp Ser Lys Pro Trp Cys Tyr Val
            180                 185                 190

Phe Lys Ala Gly Lys Tyr Ser Ser Glu Phe Cys Ser Thr Pro Ala Cys
        195                 200                 205

Ser Glu Gly Asn Ser Asp Cys Tyr Phe Gly Asn Gly Ser Ala Tyr Arg
    210                 215                 220

Gly Thr His Ser Leu Thr Glu Ser Gly Ala Ser Cys Leu Pro Trp Asn
225                 230                 235                 240

Ser Met Ile Leu Ile Gly Lys Val Tyr Thr Ala Gln Asn Pro Ser Ala
                245                 250                 255

Gln Ala Leu Gly Leu Gly Lys His Asn Tyr Cys Arg Asn Pro Asp Gly
            260                 265                 270

Asp Ala Lys Pro Trp Cys His Val Leu Lys Asn Arg Arg Leu Thr Trp
        275                 280                 285

Glu Tyr Cys Asp Val Pro Ser Cys Ser Thr Cys Gly Leu Arg Gln Tyr
    290                 295                 300

Ser Gln Pro Gln Phe Arg Ile Lys Gly Gly Leu Phe Ala Asp Ile Ala
305                 310                 315                 320

Ser His Pro Trp Gln Ala Ala Ile Phe Ala Lys His Arg Arg Ser Pro
                325                 330                 335

Gly Glu Arg Phe Leu Cys Gly Gly Ile Leu Ile Ser Ser Cys Trp Ile
            340                 345                 350

Leu Ser Ala Ala His Cys Phe Gln Glu Arg Phe Pro Pro His His Leu
        355                 360                 365
```

-continued

```
Thr Val Ile Leu Gly Arg Thr Tyr Arg Val Val Pro Gly Glu Glu
    370                 375                 380

Gln Lys Phe Glu Val Glu Lys Tyr Ile Val His Lys Glu Phe Asp Asp
385                 390                 395                 400

Asp Thr Tyr Asp Asn Asp Ile Ala Leu Leu Gln Leu Lys Ser Asp Ser
                405                 410                 415

Ser Arg Cys Ala Gln Glu Ser Ser Val Val Arg Thr Val Cys Leu Pro
            420                 425                 430

Pro Ala Asp Leu Gln Leu Pro Asp Trp Thr Glu Cys Glu Leu Ser Gly
        435                 440                 445

Tyr Gly Lys His Glu Ala Leu Ser Pro Phe Tyr Ser Glu Arg Leu Lys
    450                 455                 460

Glu Ala His Val Arg Leu Tyr Pro Ser Ser Arg Cys Thr Ser Gln His
465                 470                 475                 480

Leu Leu Asn Arg Thr Val Thr Asp Asn Met Leu Cys Ala Gly Asp Thr
                485                 490                 495

Arg Ser Gly Gly Pro Gln Ala Asn Leu His Asp Ala Cys Gln Gly Asp
            500                 505                 510

Ser Gly Gly Pro Leu Val Cys Leu Asn Asp Gly Arg Met Thr Leu Val
        515                 520                 525

Gly Ile Ile Ser Trp Gly Leu Gly Cys Gly Gln Lys Asp Val Pro Gly
    530                 535                 540

Val Tyr Thr Lys Val Thr Asn Tyr Leu Asp Trp Ile Arg Asp Asn Met
545                 550                 555                 560

Arg Pro
```

UNITED STATES PATENT AND TRADEMARK OFFICE
CERTIFICATE OF CORRECTION

PATENT NO. : 10,160,813 B2
APPLICATION NO. : 14/762601
DATED : December 25, 2018
INVENTOR(S) : Guy Reed It is certified that error appears in the above-identified patent and that said Letters Patent is hereby corrected as shown below:

In the Specification

At Paragraph 2, Lines 1 through 5, please delete the following statement:
"STATEMENT OF GOVERNMENT RIGHTS
The present invention was made with United States government support under Grant Number HL58496, HL92750 and NS073147 (GR) awarded by the National Institutes of Health Grants. The government has certain rights in the invention."

Please add the following statement:
-- STATEMENT OF GOVERNMENT RIGHTS
This invention was made with Government support under Grant Numbers HL058496, HL097250, and NS073147 awarded by the National Institutes of Health. The U.S. Government has certain rights in the invention. --

Signed and Sealed this
Fourth Day of June, 2019

Andrei Iancu
*Director of the United States Patent and Trademark Office*